United States Patent [19]
Kelly et al.

[11] 4,237,574
[45] Dec. 9, 1980

[54] TOOTH CLEANING APPARATUS

[76] Inventors: J. Robert Kelly, 1220 Chambers Rd., Apt. 403A, Columbus, Ohio 43212; Mark J. Squicquero, 6094 Busch Blvd., Apt. 93, Columbus, Ohio 43229

[21] Appl. No.: 931,751

[22] Filed: Aug. 7, 1978

[51] Int. Cl.$^3$ .................. A46B 13/02; A61H 7/00
[52] U.S. Cl. .................. 15/167 A; 15/21 R; 128/62 A
[58] Field of Search .......... 15/167, 167 A, 110, 15/21 R; 128/24 A, 66, 172.1, 62 A

[56] References Cited

U.S. PATENT DOCUMENTS

| | | | |
|---|---|---|---|
| 1,818,146 | 8/1931 | Maker | 128/62 A X |
| 3,109,192 | 11/1963 | Levenson | 15/167 A |
| 3,380,446 | 4/1968 | Martin | 128/172.1 X |
| 3,401,690 | 9/1968 | Martin | 128/172.1 |
| 3,502,076 | 3/1970 | Bertoli | 128/172.1 |
| 3,731,675 | 5/1973 | Kelly | 128/62 A |
| 3,847,662 | 11/1974 | Massa | 128/62 A |
| 4,011,616 | 3/1977 | Kennedy | 15/21 R |
| 4,144,882 | 3/1979 | Takemoto et al. | 128/172.1 |

*Primary Examiner*—Edward J. McCarthy
*Attorney, Agent, or Firm*—Robert E. Stebens

[57] ABSTRACT

A tooth cleaning apparatus is provided having a structurally rigid tray including a U-shaped channel for the reception therein of teeth carried by a jaw member. The cleaning means is also included in associated relationship with the tray. Secured to the outer surface of the tray at a point opposite the open side thereof are resilient pads of predetermined length to enable mechanical interengagement with the teeth to effect securing of the tray to the opposite jaw member from the teeth being cleaned. Included within the interior of the U-shaped channel are a predetermined number of stop elements positioned to limit the depth to which the jaw may be inserted and to assure proper alignment of the teeth and sulcus with the tray. In one embodiment of the apparatus, the interior of the U-shaped channel is provided with a plurality of brush bristles to effectuate brushing the teeth as well as cleaning the sulcus. Another embodiment of the apparatus has cleaning means which include ultrasonic energy producing mechanisms. An embodiment utilizing ultrasonic energy effects cleaning through the movement of the brush bristles relative to the tooth surfaces, whereas the embodiment without ultrasonic energy achieves the cleaning operation through a mechanical chewing function performed by the person. In a further variation of the apparatus, fluid conducting means are provided for transmitting ultrasonic energy from the producing devices to the surfaces of the teeth and to the region of the sulcus.

7 Claims, 14 Drawing Figures

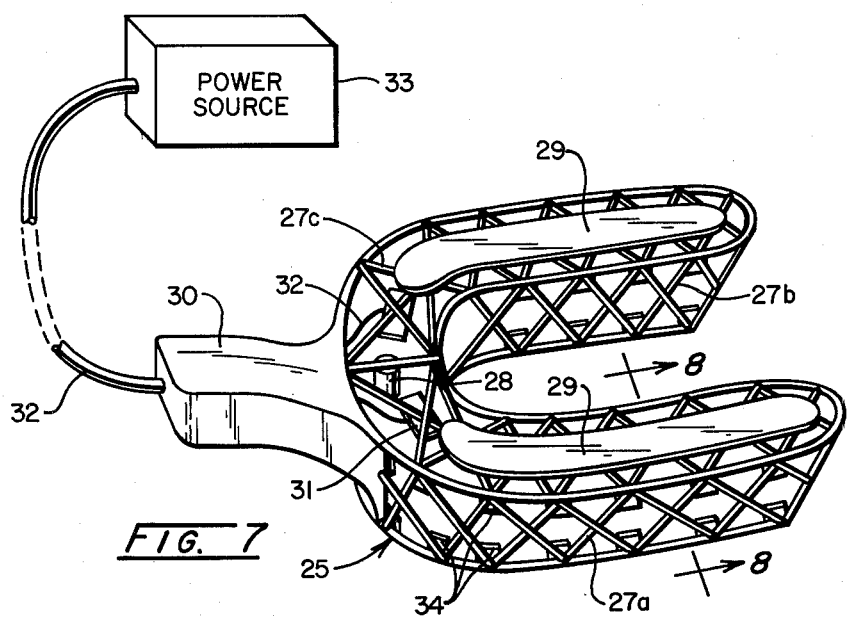
FIG. 7
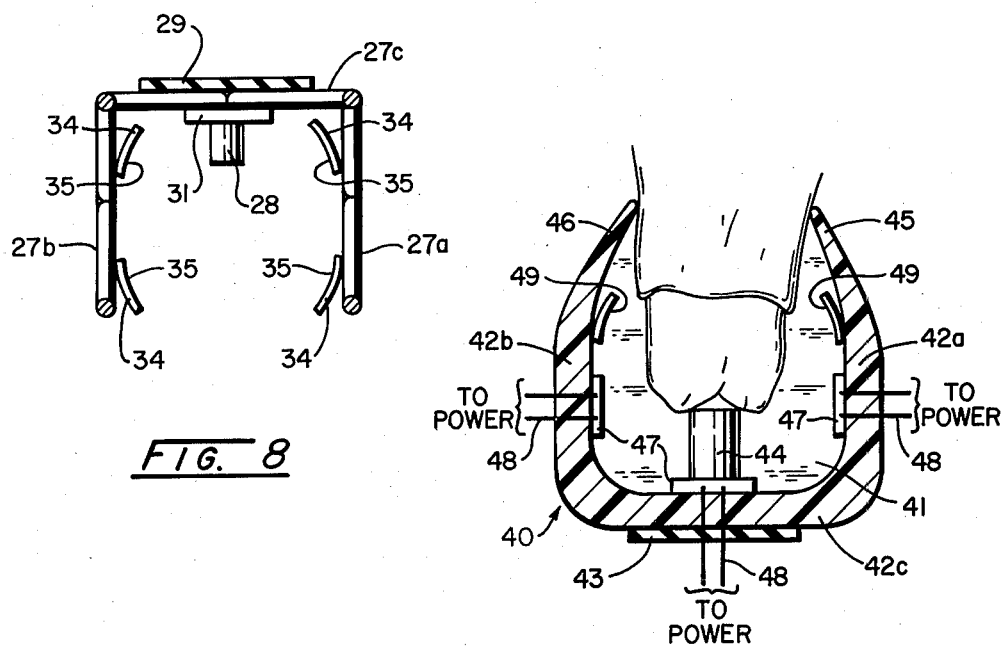
FIG. 8
FIG. 9

TOOTH CLEANING APPARATUS

BACKGROUND OF THE INVENTION

This invention relates to tooth cleaning apparatus and it specifically relates to an improved construction and cleaning mechanisms that provide consistently improved brushing for all persons. It relates even more particularly to apparatus that can be utilized by physically handicapped persons, such as those without hands or those without ability to utilize the hands, in effectively brushing their teeth without the assistance of other persons.

A traditional toothbrush generally consisting of a long narrow flat construction, one end thereof having bristles extending perpendicularly from one of the flat surfaces, is only as effective as the person using it. This traditional brush structure has proven ineffective over the years as its use often requires a thoroughness and manual dexterity that eludes many average users having normal manual dexterity either because of the user's impatience or lack of muscle coordination.

The jaw structure itself places other limitations upon such conventional dental hygiene methods and techniques. The mandible presents special problems for either electric or manual toothbrushing as it is not as stable as the maxilla.

This conventional means of dental hygiene, which many people having no physical problems cannot seem to master consistently with effectiveness, places the physically or mentally handicapped at an incredible disadvantage. The generally poor oral health of the handicapped population has been well documented. Various toothbrush designs have been proposed to eliminate these inherent limitations in the conventional dental hygiene method, but none have performed adequately to achieve an entirely acceptable degree of effectivity. Consequently, in the case of handicapped persons, it is frequently necessary to provide those persons with assistance.

Regarding the handicapped, toothbrushes of a design commonly known as a "chewing toothbrush" have been devised but failed to achieve the intended objectives because, in addition to a chewing action, they required an exterior supporting or manipulating force such as application of force by a person's hand through a handle section to effectuate a brushing action. In most instances, the handicapped are incapable of properly applying such a force, if they can apply such a force at all. The present invention requires only a chewing action with respect to one embodiment thereof and no action on the part of the person to effectuate a proper brushing of the teeth.

Additionally, previous chewing toothbrush designs comprising both rigid and resilient mouth pieces have not been found satisfactory because they have not provided the proper brushing action of the teeth. Some previous designs provided dual-sided, brush channels for simultaneous brushing of both the upper and lower teeth simultaneously. However, these dual-sided brushes do not necessarily operate in the same degree or manner with respect to the opposite jaws or the teeth carried thereby. The resiliency of the bristles may be slightly different or the configuration of the teeth may be different so that a greater or lessor degree of brushing effectiveness is obtained with respect to one jaw and the brush may be maintained in a more or less fixed position with respect to the other. This possible disadvantage in operation would only be apparent in the brushing action obtained by a chewing action or alternate opening and closing of the jaws.

Finally, previous chewing toothbrush designs have not been accepted and utilized because they provided no means to assure proper brush contact with the sulcus as well as the teeth of the user. Rather than providing gingival stimulation, the prior devices often provided "toothbrush truma" to the gums. Scuffing of the gingiva often occurred from the use of the previous toothbrush designs because they comprised no means to control how far the teeth were inserted into their respective bristle channels nor did they provide proper bristle angles within the bristle channels with respect to the surfaces of the teeth inserted therein.

SUMMARY OF THE INVENTION

An important objective of this invention is to provide a tooth cleaning apparatus of a chewing toothbrush-type comprising a structurally rigid tray adapted to conform to a jaw member and which will enable a user to simultaneously cleanse and brush all of the teeth of one jaw member with proper procedure utilizing only the muscles used in mastication. This invention provides a toothbrush comprising a U-shaped mount piece or tray formed from a suitable material having the necessary characteristics of structural rigidity and configured to receive all of the teeth of one jaw member along with the immediately adjacent portions of that jaw. The tray is formed with an outwardly opening U-shaped channel having the interior thereof covered with brush bristles distributed over substantially the entire surface thereof to effectuate the cleansing of the teeth and sulcus of the jaw member inserted therein. The exterior surface of the rigid tray, at its upper surface, is provided with a resilient elastomeric material designed to mechanically interengage with the teeth on the opposite jaw, thus maintaining the tray in a relatively fixed position with respect to that jaw while relative movement between the jaws will then effect a brushing action as to those teeth then positioned within the bristles covered channel of the tray.

The tray includes a plurality of stop elements disposed in the channel which receives the jaw portion and teeth carried thereon that are to be brushed. The teeth of the user are inserted into the bristle channel until reaching a depth where the teeth mechanically engage respective ones of the stop elements located at predetermined locations within the bristle channel and which may be formed from the same material as the tray or may possess a degree of resilience for cushioning. These stop elements thus control the depth or extent to which the teeth can be inserted into the bristle channel to thereby enhance the effectiveness of the bristles.

The brush bristles within the channel may be molded into the channel walls for mechanical support and are preferably positioned at predetermined angles throughout the channel so the bristles may most advantageously contact the teeth and sulcus of the user when the teeth of the jaw being inserted into the tray channel mechanically engage the rubber stop elements.

Secured to the outer surface of the tray in opposed relationship to the open channel thereof are resilient pads of predetermined length to enable mechanical engagement with a sufficient number of teeth of the opposite jaw during brushing operations to secure the structure in a relatively fixed relationship to the jaw opposite that having the teeth being brushed. Thus, when the teeth of the jaw to be brushed are inserted into the bristle channel to the point where they mechanically engage the stop elements and when the teeth of the opposite jaw mechanically engage the resilient pads, the tray is maintained in a substantially fixed position with respect to that jaw thus enabling relative movement between the jaws to effect the proper brushing action as to those teeth when positioned within the bristle-filled channel. During actual brushing, the teeth do not necessarily engage the stop elements in lateral movement, but the teeth will be effectively limited in their depth of penetration or insertion into the channel by contact with the stop elements.

Another important objective of this invention is to provide an embodiment of the tooth cleaning apparatus which is of the described construction wherein the toothbrush incorporates a suitable power source, such as one or more ultrasonic transducer elements, to effect a vibratory action to properly brush and cleanse the teeth of the jaw inserted into the bristle channel. An ultrasonic transducer element forming a cleaning means power source is embedded within the body structure of the tray, with the transducer element being connected by suitable power transmission means to an external power source that is selectively operable for energization of the transducer element. As in the case with the manual brushing technique as previously described, when the teeth of the jaw to be brushed are inserted into the channel to the point where they engage the stop elements and in contacting engagement with the bristles, and when a sufficient number of teeth of the opposite jaw mechanically engage the resilient pads thereby cooperatively maintaining the tray in a relatively fixed position, the vibrator action produced by the transducer element effects a proper brushing action as to those teeth then positioned within the channels as well as effecting cleansing of the sulcus.

Alternative embodiments of the tooth cleaning apparatus incorporating powered cleaning means, such as the ultrasonic transducer elements, are also provided in accordance with this invention. These alternative embodiments include the incorporation of a fluid medium for effecting the mechanical coupling of an ultrasonic energy source with the tooth surfaces and associated sulcus of the adjacent supporting jaw member. One form of an embodiment of this type utilizes a tray of U-shaped chanel configuration but having wall sections that are of open mesh construction to permit interflow of the fluid having a suitable ultrasonic energy transmitting characteristic with a quantity thereof contained in the mouth. One or more transducer elements are supported on the open mesh tray in immersed relationship to the fluid medium and are operable in effective generation of ultrasonic energy that is then transmitted into operative relationship with the teeth thereby producing an extremely effective cleaning operation.

Another form of an embodiment of the apparatus incorporating ultrasonic cleaning means has a tray of U-shaped channel configuration that is impervious to the fluid medium for energy transmission. Furthermore, the tray has the channel thereof designed so that the sidewalls will be positionable in fluid sealing engagement with the surfaces of the jaw member immediately adjacent the base of the teeth but enclosing the sulcus within the interior of the channel. Ultrasonic transducer elements are mounted interiorly of the channel to be immersed within a fluid energy transmitting medium in direct coupled relationship thereto. This form of the apparatus is of particular advantage in that the power requirements are materially reduced in comparison to the power requirements of the open mesh form as a consequence of the substantially reduced quantity of the fluid energy transmitting medium which is involved.

Enhancement of the cleaning operation obtained with either the open mesh or sealed tray embodiments of the tooth cleaning apparatus can be achieved with reflector devices that are operative with respect to ultrasonic energy transmitted by a fluid medium. Appropriate reflector devices may be disposed in selected relationship to the several ultrasonic transducer elements and the teeth to redirect ultrasonic wave energy that may have been initially travelling away from the teeth, in a direction to be effective in performance of the cleaning function. Proper selection and location of such reflector devices as well as appropriate configuration of their reflective surfaces will result in a substantial improvement of the effectiveness and efficiency of such apparatus in performance of a cleansing operation. It will be particularly advantageous in enabling the design of apparatus that is highly capable of removing debris and food particles from the sulcus.

A further embodiment of the tooth cleaning apparatus incorporating ultrasonic cleaning means provides a tray of U-shaped channel configuration which is coupled by fluid conduits to an external ultrasonic energy generating device. Ultrasonic energy is thus transmitted by this fluid medium to the interior of the tray channel where it is effective in performance of a cleansing operation. The tray may be of a construction that either forms a fluid sealing engagement with the jaw member thus containing the fluid medium in relationship to the jaw and teeth or does not form such a fluid seal thereby permitting fluid to fill the mouth. This embodiment may also alternatively be of a static type or of continuous circulating type. In the former, the fluid medium is merely caused to fill the tray's channel or the person's mouth and functions solely as an ultrasonic energy transmitting means. In the latter, fluid is caused to circulate into the tray and is then removed from either the tray or mouth where it may be either disposed of or it may be filtered to remove debris and food particles entrained therein as a result of the cleaning operation and then recycled through the system.

A further embodiment of the tooth cleaning apparatus utilizing ultrasonic energy has the ultrasonic energy generating device and transducer located externally to the tray. Energy conduit means is provided for mechanically transmitting the energy to a terminal coupling end portion carried by the tray for effecting transfer of energy to a fluid contained either in the mouth or within only the tray channel to thereby effect a cleaning operation.

It is an important object of this invention to provide tooth cleaning apparatus of the described construction wherein proper and effective brushing action is obtained using only the muscles utilized in mastication or by using a transducer element incorporated in, or associated with, the structure. Providing of a transducer element activated by ultrasonic energy from a suitable outside power source such that the structure can be readily and efficiently utilized by the physically and mentally handicapped who are otherwise unable to adequately utilize a conventional toothbrush or to use the toothbrush of this invention by means of this masticating muscles.

A still further object of this invention is to provide tooth cleaning apparatus of the brush type, or ultrasonic transducer type, having a construction as described herein where the bristles, transducers, or reflectors contained within the tray channel are oriented with respect to the teeth and sulcus in a manner determined by the dentist to be most appropriate for any particular patient. The dentist has control over bristle densities and bristle pressures thus minimizing any potential for "toothbrush trauma". Thus, each cleaning apparatus can be custom fitted to the patient's arch and tooth form for maximum cleaning and gingival stimulation.

These and other objects and advantages of this invention will be readily apparent from the following detailed description of embodiments thereof and the accompanying drawings.

DESCRIPTION OF DRAWING FIGURES

FIG. 7 is a perspective view of modified form of the apparatus including an electronic-mechanical transducer.

FIG. 8 is a vertical sectional view on an enlarged scale taken along line 8—8 of FIG. 7.

FIG. 9 is a vertical sectional view on an enlarged scale of a modified form of the apparatus shown in FIG. 6 as would be seen along a section line 9—9 of such modified FIG. 6.

DESCRIPTION OF THE ILLUSTRATED EMBODIMENT

Figure 1:
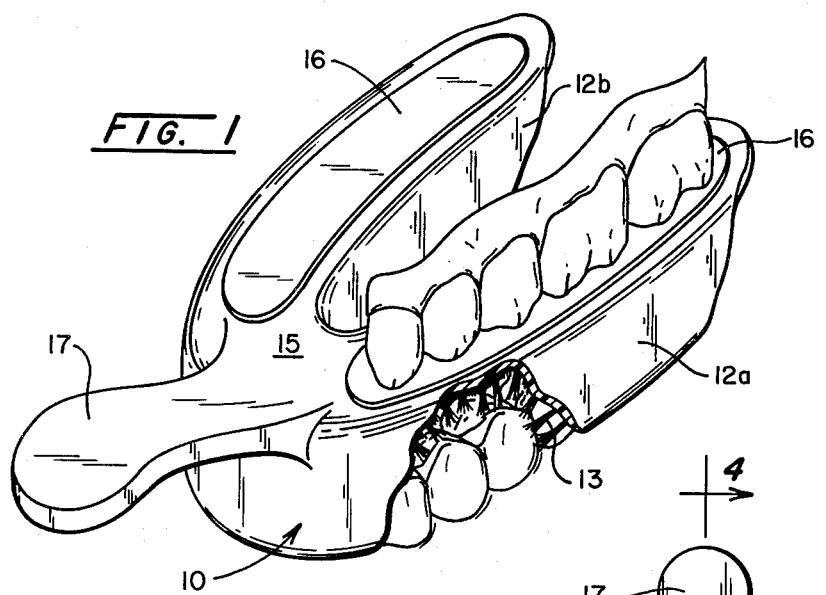
FIG. 1 is a perspective view, with a portion broken away, of a brush-type tooth cleaning apparatus constructed in accordance with this invention and showing a number of teeth to illustrate the interaction between the teeth and brush bristles.
Figure 2:
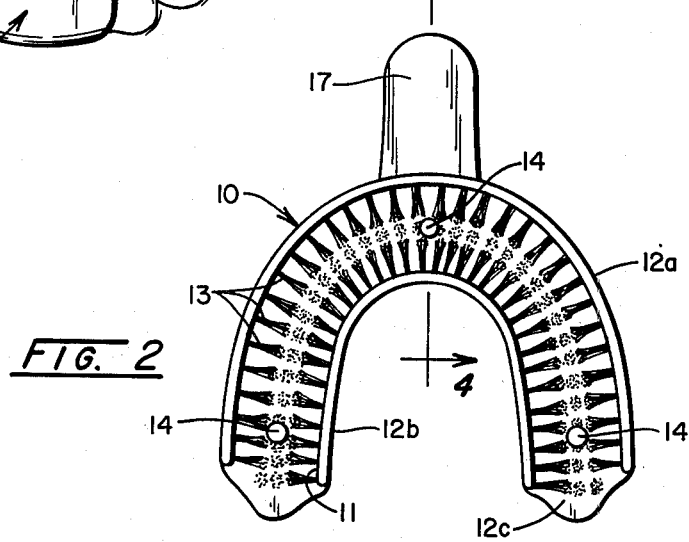
FIG. 2 is a bottom plan view thereof.

As shown in FIGS. 1 and 2, a brush-type tooth cleaning apparatus of this invention, and hereinafter designated for convenience as a toothbrush, comprises a structurally rigid U-shaped tray 10 adapted to conform to a jaw. Tray 10 is preferably molded of colored acrylic but nearly any sufficiently structurally rigid material safe for insertion into the mouth would be suitable.

Figure 4:
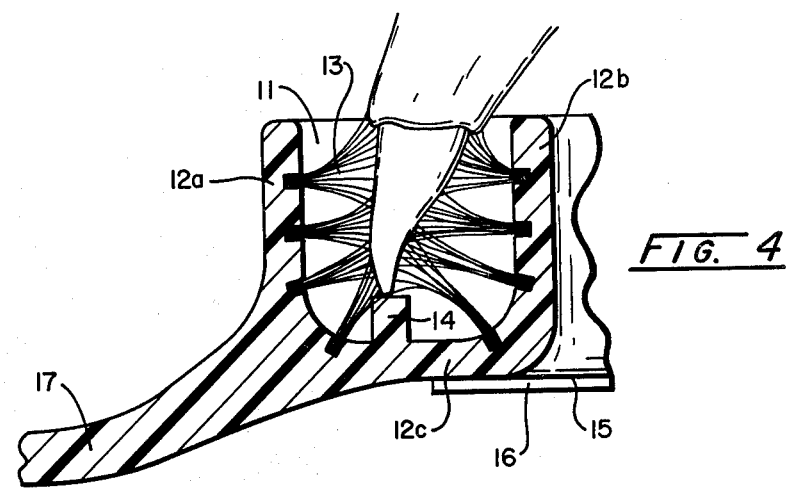
FIG. 4 is a fragmentary vertical sectional view on an enlarged scale taken along line 4—4 of FIG. 2, but illustrated as operatively positioned on a jaw.
Figure 5:
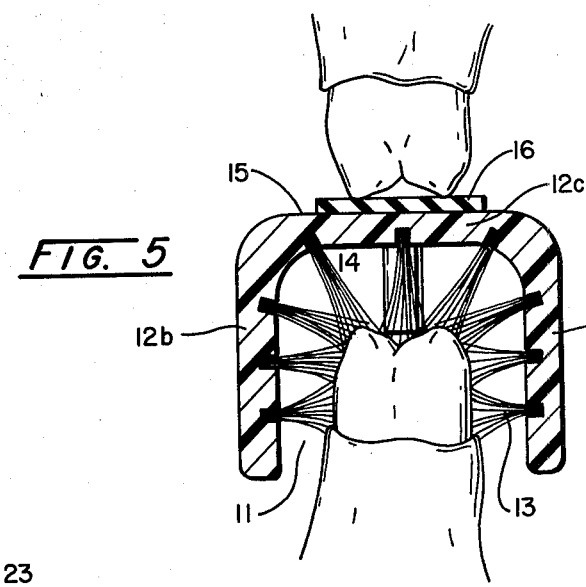
FIG. 5 is a vertical sectional view on an enlarged scale taken along line 5—5 of FIG. 3.

As shown most clearly in FIGS. 2, 4 and 5, tray 10 has an outwardly opening U-shaped channel 11 extending around the periphery thereof. This channel 11 includes two generally vertical walls 12a and 12b and interconnecting transverse wall 12c. Molded into the channel walls 12a, 12b, and 12c of tray 10 and extending interiorly of the channel are a plurality of tufts of conventional type brush bristles 13 which form tooth cleaning means. Tray 10 is preferably molded to fit the arch and tooth form of a particular user to facilitate maximum cleaning and gingival stimulation. Thus, walls 12a and 12b are of sufficient length and the transverse wall 12c of sufficient width such that when the teeth of the jaw to be brushed of a particular user are inserted into channel 11, the bristles 13 extending from walls 12a, 12b, and 12c properly contact the teeth and sulcus of the jaw inserted therein. The channel 11 extending around the periphery of the tray 10 is of sufficient length such that all of the teeth of the jaw of the user inserted therein are properly contacted by the bristles 13 extending therefrom.

The brush bristles 13 are of the conventional type. As in conventional toothbrushes, these bristles are gathered into tufts, the bases of which are molded into channel walls 12a, 12b and 12c. These brush bristles 13 preferably extend outwardly from the surfaces of channel walls 12a, 12b and 12c at various predetermined angles throughout channel 11, thus forming a generally contiguous brushing surface as shown in FIG. 2. The angles of extension of the various bristles 13 from surfaces of the walls 12a, 12b and 12c are predetermined by a dentist, with those various angles of projection being selected for purposes which will be further described.

Also contained within channel 11 are a predetermined number of stop elements 14 extending generally perpendicularly from the transverse wall 12c and attached thereto. These stop elements are preferably integrally molded into the wall 12c but any conventional attachment means can be utilized. The stop elements 14 of the present invention are constructed of nearly uncompressible hard material such as that of the tray but any similar material having the desired characteristics can be utilized to provide the necessary mechanical stop to effectively limit the depth to which the jaw may be inserted in the channel. Each stop element 14 is of predetermined length and selected location within channel 11 to achieve the desired cooperation with selected ones of the teeth to thereby facilitate the initial proper positioning of the tray on the jaw.

The number of stop elements 14 and their length and location, as well as the angles of projection of the various brush bristles 13 extending outwardly from surfaces of the channel walls 12a, 12b and 12c, are determined by a dentist so that the various brush bristles 13 form proper dental contact with the teeth and sulcus of the specifically intended user when the stop elements 14 are mechanically engaged by the respective teeth of the jaw being inserted into bristle channel 11. FIGS. 4 and 5 show proper bristle contact with the teeth and sulcus as would occur when the teeth of one jaw are inserted into the bristle channel 11 until certain specific teeth thereof mechanically engage the stop elements 14 contained within bristles channel 11. As shown in FIG. 4, the mechanical contact of certain specific teeth with the stop elements 14 prevents further insertion of the teeth and adjacent portions of the jaw into bristle channel 11.

Figure 3:
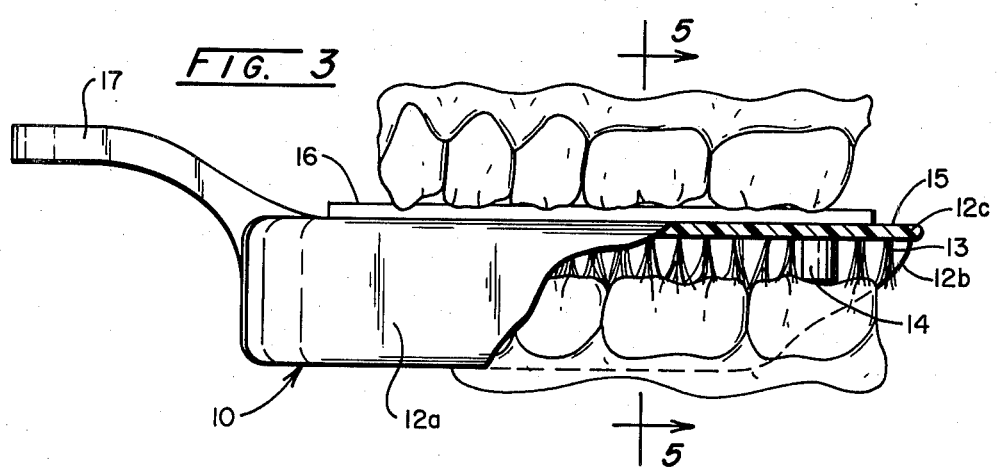
FIG. 3 is a side elevational view of the apparatus with a portion broken away and with a number of teeth being shown diagrammatically to illustrate the interaction between the teeth and brush bristles.

Secured to the outer surface 15 of the tray 10 are resilient pads 16. The pads 16 are constructed of any suitable material having the desired yieldable, resilient characteristics, such as rubber, and may be adhesively bonded to the tray surface. These resilient pads 16 are preferably of a predetermined length to enable mechanical engagement with a sufficient number of teeth of the jaw not being brushed (or the jaw itself) to secure tray 10 in a relatively retained relationship to the jaw opposite that having teeth being brushed. This mechanical engagement of a number of teeth of the one jaw with the resilient pads 16 is shown in FIGS. 1, 3 and 5.

Thus, when the teeth of the jaw to be brushed are inserted into the bristle channel 11 to the point where certain specific teeth thereof mechanically engage the respective stop elements 14, and when a sufficient number of teeth of the opposite jaw mechanically engage the resilient pads 16, the tray 10 is maintained in a relatively retained or fixed position with respect to the one jaw thereby enabling relative movement between the jaws to effect the proper brushing action as to those teeth then positioned within the bristle channel. As will be understood by reference to FIG. 4, during actual brushing the teeth do not necessarily engage the stop elements in any lateral movement, but will be effectively limited in up and down movement by contact with the stop element 14 to prevent possible injury to the gingival region.

An elongated projection forming a handle 17 extends outwardly and upwardly from the exterior surface 15 of tray 10 from the forwardly facing apex of the U-shaped tray. This handle is conveniently integrally molded as part of tray 10 and is of a size and shape to facilitate the handling, storage and the insertion and removal of the brush with respect to a person's mouth. The handle 17 is not utilized during brushing operations as the brushing function is performed utilizing only the mastication muscles but the handle may be adapted for specific auxiliary mechanisms or support structure to facilitate utilization by handicapped persons.

This embodiment of the present invention is preferably custom made to fit the arch and tooth form of a particular user. In this embodiment, the angles of the bristles 13 extending from the surface of the channel walls 12a, 12b and 12c and the number, location and length of stop elements 14 are all preferably determined by a dentist so that the various brush bristles 13 form a proper and preferred dental contact with the teeth and sulcus of the user when the teeth of the jaw to be brushed are inserted into the bristle channel 11 the extent of insertion is limited by certain specific teeth engaging the stop elements 14. At this point, as shown in FIG. 4, the teeth of the user are prevented from further insertion into the channel thus limiting the degree of compression of the bristles and the amount that the bristles may project onto the gums thus minimizing gingival abrasion. However, the bristle angles and lengths are such that they will project far enough into the sulcus of the user to remove any food particles, plaque, pathologic debris or any other undesired foreign matter simply by the in and out and the lateral movement of the teeth with respect to the bristle channel 11.

While the tray 10 can be molded of a standard size with standard bristle angles and standard stop element locations and sizes such that one tray can be utilized by nearly everyone, a custom fitted tray as previously described achieves the maximum possible cleansing action while minimizing the effects of toothbrush trauma. Custom fitting can be achieved by a relatively simple and inexpensive procedure and techniques.

In accordance with this method, dental impressions are first taken of a patient's teeth. From the impressions a cast of the jaw is made. Both impressions and cast are made using conventional dental methods well known in the art. The cast of the teeth of the jaw of the patient is then reduced uniformly in size by removing approximately a 1 millimeter surface layer to obtain the proper or predetermined degree of bristle compression. The bristles are then mounted on the cast of the jaw such that they just contact the teeth and sulcus forming a proper dental contact with the teeth and sulcus. Mounting at this time is of a temporary nature and can be effected by a suitably cohesive material which may be readily removed upon completion of the fabrication procedure.

The cohesive material is molded around the bristles, and the underlying cast of the teeth, to a depth where only the end portions of the bristles that are to be embedded in the tray remain exposed. At this point, a suitable acrylic material in a liquid state is poured or cast with the bristles in an appropriately configured mold. This acrylic material is then permitted to harden, either by time alone or in conjunction with techniques that reduce the time required for completing the hardening. Upon completion of the hardening procedure, the bristles will then be rigidly secured in the tray and the cast of the teeth is removed along with the cohesive material initially utilized for mounting of the bristles on the tooth cast.

Stop elements 14 are then inserted as dowels or alternatively molded into tray 10 in the same step and manner of fabrication as are brush bristles 13 at optimum selected positions to engage acceptable tooth structures to ensure that the teeth of the user will be inserted into proper bristle contact. At this point, because the bristles were molded to fit a jaw cast reduced uniformly in size by approximately 1 millimeter, proper bristle compression on the surfaces of the teeth and proper bristle extention into the sulcus is obtained thus permitting the maximum possible cleansing action utilizing the present invention in the manner previously described.

Figure 6:
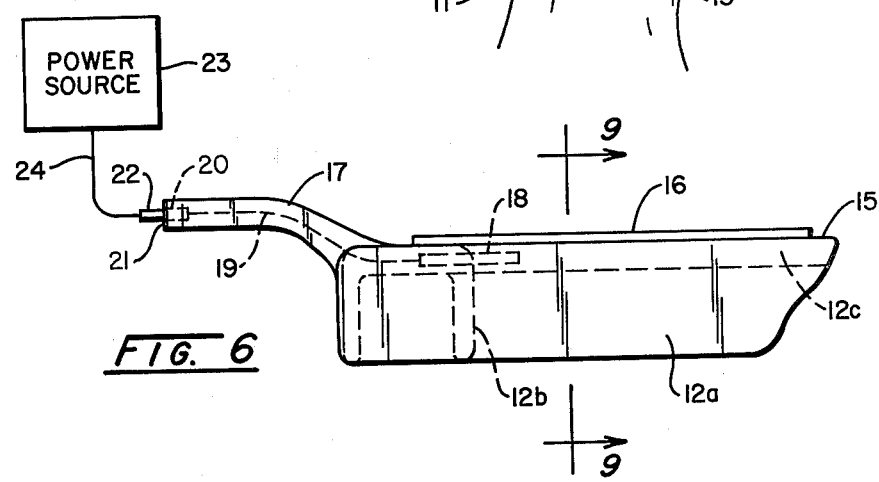
FIG. 6 is a side elevational view of another embodiment of the tooth cleaning apparatus of this invention including an electro-mechanical transducer.

FIG. 6 shows another embodiment of the tooth cleaning apparatus of this invention. In this embodiment, which comprises a structure similar to that described in conjunction with FIGS. 1–5 embedded in the transverse wall 12c at the front apex of the tray is an ultrasonic transducer element 18, such as a piezoelectric crystal which is driven by a suitable electrical power source. This ultrasonic transducer element 18, which in cooperation with the brush bristles forms the cleaning means, is located within the body of the tray 10 such that tray 10 receives the vibratory effect created by the transducer element. An electrical power transmission conductor 19 runs from the transducer element 19 through tray 10 where it is embedded in the wall 12c of the tray 10 and also extends through the handle 17, where it is also embedded, and is connected to an electrical connector socket 20. Connector socket 20 opens to the outer surfaces 21 of the handle 17 in which it is embedded beneath and is designed to receive a suitable electrical connector jack 22 which is connected to an appropriate power source 23 via power transmission conductor 24. Power transmission conductors 19 and 24, connector socket 20, ultrasonic transducer element 18 and electrical connector jack 22 are of conventional types and enable disconnection of the components.

The embodiment of this invention, as disclosed in FIG. 6, is positioned within the mouth in the same manner as the conventional embodiment. When teeth of the jaw to be brushed are inserted into the bristle channel to the point where certain specific teeth thereof mechanically engage the rubber stop elements 14 and when a sufficient number of teeth of the opposite jaw engage the resilient pads 16, the tray 10 is maintained in a relatively retained position enabling the vibratory motion created by the ultrasonic transducer element 18 activated by the outside source 23 to effect the proper brushing action as to those teeth then positioned within bristle channel 11.

While the structure disclosed in conjunction with FIG. 6 as to an embodiment of the invention utilizing ultrasonic energy for effecting the desired brushing or cleaning action is a basic apparatus therefor, it will be understood that there are advantageous variations and alternative constructions that may be utilized with ultrasonic power sources and transducer elements. To further exemplify this type of tooth cleaning apparatus, reference may be had to FIGS. 7 and 8 wherein an alternative form of a tray 25 is illustrated and is seen to have the same general overall configuration as to including a U-shaped channel for receiving the teeth of one jaw member but which does not include brush bristles. This device comprises a generally open meshed structure which is uniquely designed to permit innerflow of fluids therethrough. The objective of this particular structure is to provide a supporting framework, or structure, for one or more of the ultrasonic transducer elements which may be of the piezoelectric crystal type, and to thus support those devices in selected positions relative to particular teeth or regions of the jaw for obtaining the greatest effectivity with due consideration to the power output capabilities thereof.

As indicated, the tray 25 comprises a structure of the same general configuration as previously disclosed in conjunction with the embodiments of FIGS. 1 through 6. This structure includes a U-shaped channel 26 that is formed with spaced walls 27a and 27b that are rigidly interconnected by a transverse wall 27c to receive a jaw member therein. These wall sections are formed from a suitable material, acrylic for example, having the necessary structural rigidity when fabricated in the form of an open mesh structure such as that which is illustrated. This structure may be formed from a molded plastic material or it may be formed from a suitable hard rubber material. Molding techniques, as will be explained further, are particularly suitable for the fabrication technique in that the tray may be readily formed into a specific configuration that is particularly adapted to a specific patient's mouth or jaw conformation. Referring to FIG. 8, which is a cross-sectional view thereof, it will be seen that the structure of the tray is also provided with stop elements 28 which function in the same manner as described with the preceding disclosed embodiments. Those stop elements are effective in providing a proper positioning of the tray 25 in relationship to the supporting jaw structure and associated gingiva. Several such stop elements 28 may be provided and relatively positioned to effect the desired location and relationship of the tray to the tooth conformations. Mounted on the U-shaped channel 26 are a pair of resilient pads 29 that are designed to cooperate with the teeth of the opposite jaw during utilization to maintain the tray in a relatively fixed position with respect to the jaw which is being subjected to a cleaning operation.

Also attached to the U-shaped channel 26 is a handle 30 comprising a suitable structure that projects laterally outward from the apex of the U-shaped channel to facilitate manipulation thereof and effect insertion and removal of the device from the jaw, particularly in the case of handicapped persons.

Utilization of the structure 25, as shown in FIGS. 7 and 8, relies upon the utilization of an energy transmitting fluid medium being retained within the mouth. A suitable fluid for this purpose is water, although other fluids, such as water containing antiseptic or cleansing agents, may be employed to facilitate the cleaning operation. The energy and force for effecting the cleaning operation is obtained from one or more ultrasonic transducer elements 31 that may be positioned on and supported in fixed relationship to the U-shaped channel 26 of the tray. These transducer elements may be of an electrically energized types such as a piezoelectric crystal and are thus provided with electrical conductors 32 for interconnection with a power source 33 that may be most appropriately externally located.

Operation of the tooth cleaning apparatus illustrated in FIGS. 7 and 8 is effected through the intake of a quantity of fluid which is retained within the mouth during the operation of the device. When the fluid is retained within the mouth, the power source 33 may be energized for activation of the ultrasonic transducer elements 31. Those elements, in view of their direct intercoupled relationship with the fluid, will be effective in transmitting ultrasonic energy through the fluid which will thus act as the carrier for that energy. The energy in wave-form thus carried by the fluid will in turn be effective in operating on all surface regions of the teeth as well as on the sulcus, in accomplishing a highly effective cleaning operation. Food particles and debris that are thus dislodged through the ultrasonic energy will be carried by and suspended within the fluid during the course of the cleansing operation. At the conclusion of the operation, with the power source 33 being deenergized, the person may then remove the tray and thoroughly rinse the mouth to thus completely dislodge and eliminate all of the food particles and debris that were thus removed by the ultrasonic energy transducers through the energy transmitting fluid medium.

To further enhance the effectivity and efficiency of the apparatus, as disclosed in FIG. 7, the tray 25 may be provided with a plurality of reflector elements 34 with those reflectors being secured and supported on the wall 27a, b and c in predetermined relationship to the several respective ultrasonic transducer elements 31. These reflector elements 34 are formed from a material that is selected for its advantageous characteristics in reflecting ultrasonic energy with minimal absorption of that energy. These reflectors are provided with specifically configured surfaces 35 that are formed in accordance with the patient's tooth and jaw conformations with the locations thereof optimumly determined in accordance with the physical relationship to a particular transducer element 31 with which the reflector is to be associated. A prime objective of the reflectors and their location as well as configuration of the surfaces 35 thereof, is to better direct the ultrasonic wave energy carried by the fluid medium into the region of the sulcus for a more advantageous and efficient effectivity in the dislodgement of food particles and other debris that may be retained within that critical region. Several such reflectors 34 may be utilized in conjunction with any specific transducer element with these reflectors being located at various positions within the interior of the wall of the U-shaped channel 26. As a specific example of the utilization of such reflectors 34, it will be noted that four such reflectors are shown secured to the channel walls 27a and 27b so that the wave energy, as carried by the fluid medium, will be reflected in a plurality of directions toward the surface areas of the adjacent teeth as well as the sulcus. For this purpose, not only are a pair of reflectors 34 positioned at the base of the channel in close relationship to the transverse wall 27c for redirecting the energy in the direction of the teeth, but to also provide a pair of reflectors at the relatively open end of the channel. These latter reflectors will thus be seen as positioned to be in more effective relationship to the sulcus region in efficiently re-directing the wave energy toward that region and prevent its relatively useless escape to the surrounding areas and regions of the mouth.

A still further embodiment of the apparatus utilizing ultrasonic energy is illustrated in FIG. 9. FIG. 9 is a cross-sectional view of an apparatus having a basic structural configuration similar to that illustrated in FIG. 6 with FIG. 9 being referenced to FIG. 6 to locate the FIG. 9 sectional view for purposes of reference. One important distinction between the modified structure of FIG. 9 and the structure shown in FIG. 6, is that the FIG. 9 structure does not include brush bristles. Also, the FIG. 9 structure further differs in that the transducer elements are not embedded in the wall structure. Accordingly, the basic configuration of the structure will be understood to comprise a tray 40 which includes a generally U-shaped channel 41. This channel 41 also includes, as seen in FIG. 9, the spaced vertical walls 42a and 42b, that are interconnected by a web portion 42c to receive a jaw member therein. Also, for purposes of retaining the tray 40 in operative relationship to a particular jaw, as in the case of the other embodiments, the outer surface of the transverse wall 42c is provided with a pair of resilient pads 43 that extend for selected distances along the exterior surface of the tray. These resilient pads 43 are operative, as in the case of the embodiment shown in FIG. 6, to effect a proper retention of the tray 40 in a predetermined relationship to an opposing jaw element and thus facilitate utilization of the device. To further effect the proper positioning of the tray in relationship to a respective jaw member, the interior of the channel 41 is provided with a plurality of stop elements 44.

The tray 40 of this embodiment, however, has the wall sections 42a and 42b formed with a relatively thick section, and thus having substantial structural rigidity, but which terminate at their outer free ends in relatively thin section, tapered marginal edge portions 45 and 46. These relatively thin-section, edge portions thus have a greater degree of flexibility and, through the appropriate configuration of the wall sections, are directed into contacting engagement with the supporting jaw structure and in particular to the gingival area immediately adjacent to but not in affecting relationship to the sulcus. The object of this particular construction is to form a tray 40 that can be effectively sealed with respect to the jaw member and thus retain fluid with the interior cavity of the U-shaped channel 41.

The purpose of a fluid sealing capability of the channel 41 relative to the jaw member is to thus enable one to fill the channel with a fluid member that is capable of transmitting ultrasonic energy and to thus permit an ultrasonic transducer element, or elements, 47 directly immersible in the fluid medium thereby forming in cooperation, cleaning means to produce the necessary energy in effecting a cleansing operation. The one or more ultrasonic transducer elements 47 may again advantageously comprise piezoelectric devices with suitable electrical interconnections 48 to an appropriately designed power source (not shown) substantially in the manner as disclosed in conjunction with FIG. 6. For example, the transducer elements 47 may be secured to the inner surfaces of the transverse wall 42c at selected locations that are determined to be particularly appropriate in effecting the energy transmission to the areas and regions for achieving the optimum cleaning effectivity. One advantage of the closed type structure, as illustrated in FIG. 9 with respect to the energy transmitting fluid medium, is that there will be a substantially lessor volume of that fluid that requires the input of energy as contrasted with the structural type illustrated in FIGS. 7 and 8. Thus, the transducer elements may be of a smaller power capability and in certain instances, a lessor number of such elements may be employed to effect the desired energy input.

As indicated, the U-shaped channel 41 includes spaced walls 42a and 42b interconnected by a transverse wall 42c that are formed from a suitable material that is not highly absorptive of ultrasonic energy. Thus, the tray itself will also aid in directing the energy transmission toward the surfaces of the adjacently located teeth as well as to the sulcus of the gingival region enclosed within the channel 41. For greater effectiveity, it may be desirable in certain instances to also employ reflector elements 49 that are located interiorly of the channel 41 and are preferably supported on the interior wall surfaces of the respective walls 42a and 42b. In certain instances of construction, the reflector elements 49 are contemplated as being integrally formed in those wall sections at the appropriate points for most effective utilization in properly directing the ultrasonic wave energy.

Figure 10:
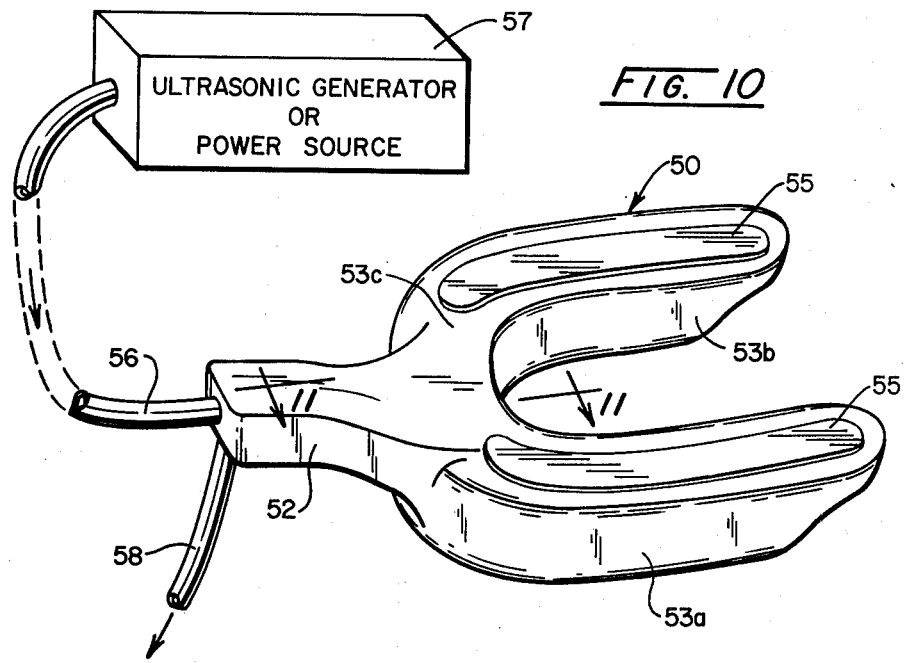
FIG. 10 is a perspective view of another embodiment of the tooth cleaning apparatus of this invention including an electro-mechanical transducer.
Figure 11:
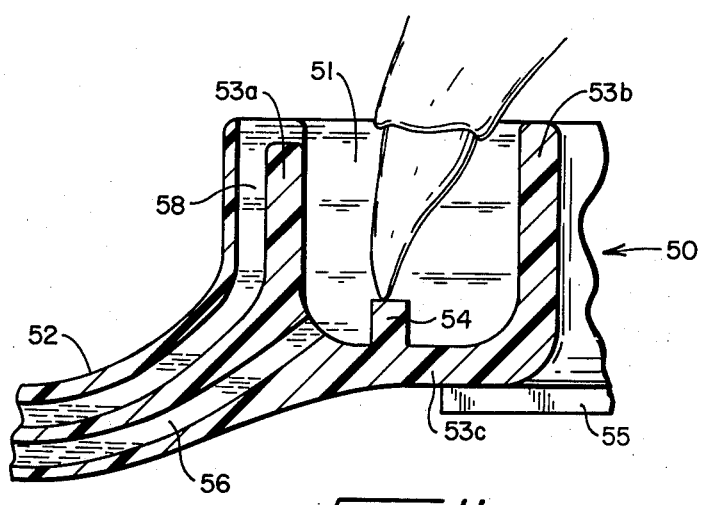
FIG. 11 is a vertical sectional view on an enlarged scale taken along line 11—11 of FIG. 10.

Another modified ultrasonic type embodiment of the tooth cleaning apparatus of this invention is illustrated in FIG. 10 and the cross-sectional view thereof (FIG. 11). The apparatus, as disclosed in those figures, comprises a tray 50 having a U-shaped channel 51 for reception of a jaw member therein and having a handle 52 integrally formed therewith in substantially the same manner as described in conjunction with FIG. 6. However, this structure also does not include brush bristles located within the channel 51. The U-shaped channel 51 includes the vertical walls 53a and 53b that are interconnected by transverse wall 53c. In this illustrative embodiment, the walls 53a and 53b are formed from a rigid material, such as a suitable plastic or rubber material, and are dimensioned to cooperate within conformity to the particular jaw member conformations. Additionally, the interior of the U-shaped channel 51 is preferably provided with one or more stop elements 54 which are arranged to maintain the walls in the desired position with respect to the teeth. Also, the exterior surface of the transverse wall 53c is provided with resilient pads 55 for cooperative mechanical interengagement with the teeth of the opposing jaw member and effecting retention of the tray in proper relationship during a cleansing operation.

Coupled with the tray 50 is an elongated flexible conduit or tube 56 which extends through the handle 52 and opens to the interior of the U-shaped channel 51.

The opposite end of the tube 56 is connected to an ultrasonic generator apparatus 57 which is externally located. This ultrasonic generator apparatus 51 is of a type which includes appropriate mechanisms and components for effecting the generation of ultrasonic wave energy in a suitable fluid medium. This fluid medium is thus directed through the tube 56 and into the tray 50. It is at this point that the fluid is then effective in transmitting the ultrasonic wave energy with respect to the teeth for effecting the cleaning operation. In the illustrative embodiment, this structure also includes a discharge conduit for removing the fluid once it has been directed into the patient's mouth. The objective of this is to then eliminate the fluid which is carrying the debris and particles that have been dislodged by the ultrasonic wave energy, to a suitable waste receptacle. Also, it is possible that the discharge conduit 58 may be interconnected into a suitable filtering system (not shown) for recycling of the same fluid through the ultrasonic generator. It will also be understood that while this particular structure and its operation is described as being of a fluid circulating type, the system may be operated in a static mode. The apparatus would then be operated by merely filling the mouth with the fluid medium and energizing the power source for the ultrasonic energy.

Figure 12:
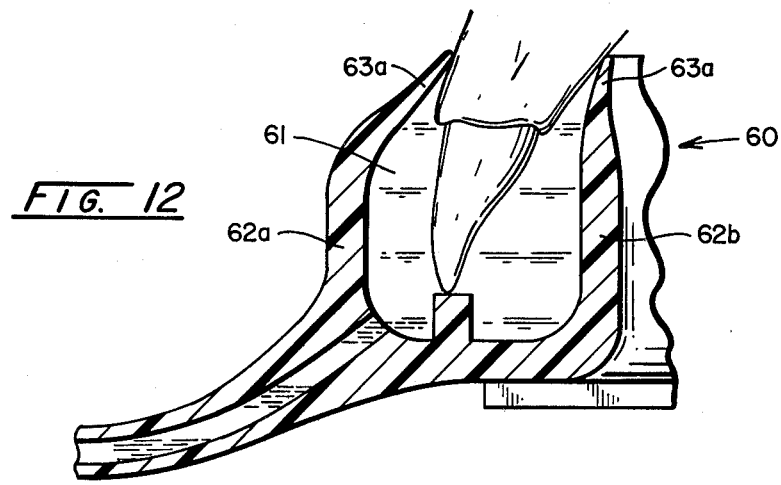
FIG. 12 is a vertical sectional view similar to that of FIG. 11 but showing a further modified structure.

As an alternative construction, the apparatus of FIGS. 10 and 11 may be constructed with a modified tray 60 and channel 61 configured and fabricated substantially in accordance with that structure illustrated and described in conjunction with FIG. 9 but as shown in FIG. 12. In this modification then the walls 62a and 62b include marginal edge portions 63a and 63b disposed in contacting engagement with the surfaces of the jaw member at a point below the intersection thereof with the teeth and thus forms a closed chamber. In this configuration, the sonic wave energy transmitting fluid may be circulated into the channel 61, as previously described, or the structure may be operated as a closed system where the fluid is merely retained within the channel until completion of a cleansing operation.

Figure 13:
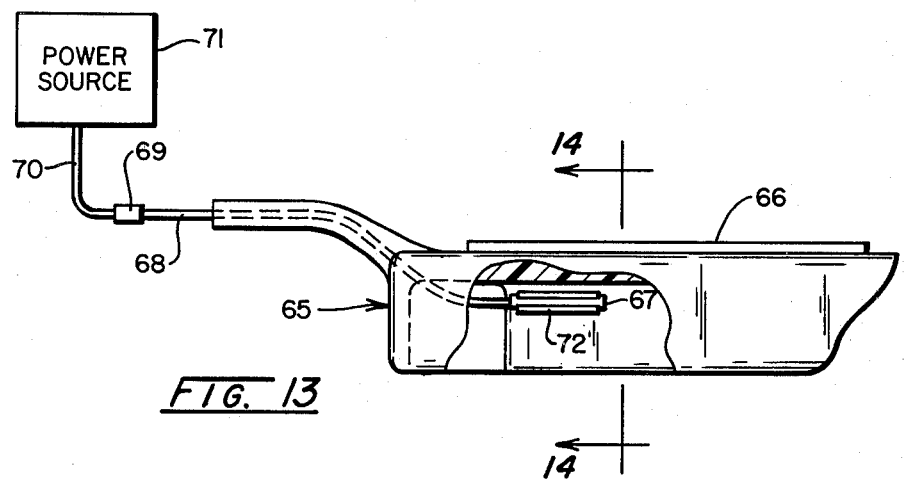
FIG. 13 is an elevational view of another embodiment of the tooth cleaning apparatus having an external ultrasonic power source.
Figure 14:
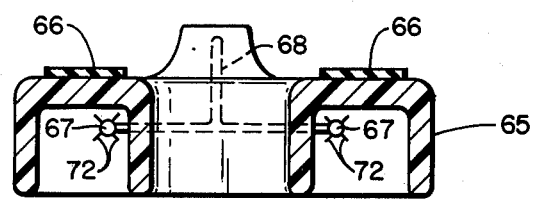
FIG. 14 is a vertical sectional view taken along line 14—14 of FIG. 13.

Another embodiment is illustrated in FIGS. 13 and 14 and is a modification of the structure disclosed in FIG. 6. In this modification, a tray 65 of the same general configuration is provided having the resilient pads 66 secured to an external surface thereof but it does not have an ultrasonic transducer element located within the tray structure nor does it include any brush bristles. Instead, a mechanical coupling element 67 is supported in fixed relationship within the channel of the tray on the end of a coupling rod 68 which projects exteriorly and serves to conduct externally generated ultrasonic energy into the interior of the tray channel. A connector device 69 secured to the end of a coupling rod extension 70 permits detachment of the coupling rod and thus enables use of a plurality of individual trays such as by the several members of a family. Ultrasonic energy is provided by an energy source 71 which incorporates a transducer (not shown) that couples with the coupling rod extension 70 and thereby resulting in mechanical transmission of the energy to the coupling element 67 through the interconnected rods 68 and 70. The coupling element 67 is preferably formed with one or more fins or plates 72 to enhance coupling with a fluid medium. Also, as can be seen in FIG. 14, a pair of similar coupling elements 67 may be provided with each element disposed within a respective portion of the tray channel. Both elements 67 are mechanically coupled to the same single coupling rod 68. It will be apparent that a greater number of coupling elements may be provided to enable the apparatus to meet specific individual requirements.

As is readily apparent from the foregoing detailed description, the tooth cleaning apparatus of this invention presents new and novel structures and which enables a person to simultaneously cleanse or brush all of the teeth of one jaw with a thoroughness and efficiency heretofore not believed obtainable. This desired, thoroughly effective brushing or cleaning action is obtained using only the muscles normally utilized in mastication or by using a transducer element intercoupled with the structural components of the apparatus with the transducer element or elements being activated by an outside power source. Thus, in addition to presenting a new and improved method of dental hygiene for physically normal persons, for the first time, means of dental hygiene is presented which can be adequately utilized by physically handicapped persons.

Having thus described this invention, what is claimed is:

1. A tooth cleaning apparatus comprising
    a structurally rigid tray of U-shaped configuration adapted to conform to a jaw member, said tray having an outwardly opening channel of U-shape extending around the periphery thereof for receiving therein teeth carried by that jaw member,
    cleaning means associated with said tray in operative relationship thereto for effecting a cleansing function with respect to teeth received within said tray, and
    retainer pads formed with said tray on the outer surface thereof, said pads being of predetermined size, said size being less than the surface area of the base of the outer surface of said tray, and positioned to enable mechanical engagement with an opposite jaw member during tooth cleaning operations to secure the structure in relatively fixed relationship to the jaw member opposite that having the teeth to be cleaned.

2. A tooth cleaning apparatus according to claim 1 wherein said tray includes at least one stop element disposed within the U-shaped channel thereof, said stop element positioned to contactingly engage a particular tooth and thereby limit the extent to which the jaw member and associated teeth may project into said tray.

3. A tooth cleaning apparatus according to claim 2 which includes a plurality of said stop elements, said stop elements being disposed in relatively spaced relationship for independent cooperative contacting engagement with respective teeth.

4. A tooth cleaning apparatus according to claim 1 which includes a handle, said handle being secured to said tray at a position to project outwardly of a person's mouth in which said apparatus may be positioned.

5. A tooth cleaning apparatus according to claim 1 wherein said cleaning means includes brush bristles mounted on the interior of said tray channel and positioned to project laterally from respective surface thereof.

6. A tooth cleaning apparatus according to claim 5 wherein said brush bristles are secured to said tray to project in predetermined relationship thereto for effecting optimum cleaning of the particular teeth.

7. A tooth cleaning apparatus according to claim 1 wherein said tray has closed channel walls.

* * * * *